(12) United States Patent
Yasui

(10) Patent No.: US 8,545,453 B2
(45) Date of Patent: Oct. 1, 2013

(54) INJECTION NEEDLE PROTECTOR, INJECTION NEEDLE UNIT, AND INJECTOR TO WHICH THIS INJECTION NEEDLE UNIT IS MOUNTED

(75) Inventor: Shinichi Yasui, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/311,696

(22) Filed: Dec. 6, 2011

(65) Prior Publication Data

US 2012/0150124 A1    Jun. 14, 2012

(30) Foreign Application Priority Data

Dec. 10, 2010   (JP) ................................. 2010-275332

(51) Int. Cl.
*A61M 5/32*   (2006.01)
(52) U.S. Cl.
USPC .............................. 604/192; 604/197; 604/198
(58) Field of Classification Search
CPC ........................................................ A61M 5/32
USPC ................... 604/192, 197, 198, 241
See application file for complete search history.

(56) References Cited

U.S. PATENT DOCUMENTS

| | | | | |
|---|---|---|---|---|
| 4,892,521 A | * | 1/1990 | Laico et al. | 604/192 |
| 4,935,016 A | * | 6/1990 | Deleo | 604/198 |
| 5,209,739 A | * | 5/1993 | Talalay | 604/195 |
| 5,385,550 A | * | 1/1995 | Su et al. | 604/110 |
| 5,403,288 A | * | 4/1995 | Stanners | 604/232 |
| 5,540,666 A | * | 7/1996 | Barta et al. | 604/192 |
| 6,478,780 B1 | * | 11/2002 | Shields | 604/263 |
| 2003/0105434 A1 | * | 6/2003 | Chang | 604/198 |
| 2006/0069347 A1 | * | 3/2006 | Besing | 604/110 |
| 2007/0255225 A1 | * | 11/2007 | Alchas et al. | 604/192 |
| 2010/0016803 A1 | * | 1/2010 | Liversidge | 604/192 |
| 2012/0010574 A1 | * | 1/2012 | Takemoto et al. | 604/192 |
| 2012/0191048 A1 | * | 7/2012 | Eaton | 604/198 |

FOREIGN PATENT DOCUMENTS

| | | |
|---|---|---|
| JP | 6-46740 | 6/1994 |
| JP | 8-191893 | 7/1996 |
| JP | 8-508182 | 9/1996 |
| JP | 2010-510513 | 4/2010 |
| WO | 2008/062285 | 5/2008 |

* cited by examiner

*Primary Examiner* — Theodore J Stigell
*Assistant Examiner* — Gerald Landry, II
(74) *Attorney, Agent, or Firm* — Wenderoth, Lind & Ponack, L.L.P.

(57) ABSTRACT

An injection needle protector protects a needle tube that is connected to a needle base and which has an outer periphery, a tip, and a needle base side opposite to the tip, by covering the needle tube. The injection needle protector includes a first cap and a second cap. The first cap protects the needle tube on the needle base side of the needle tube and has a supporter that supports the needle tube from the outer periphery of the needle tube. The first cap further has a held portion at an outer periphery of the first cap for being held by a fixing portion of an injector holder. The second cap protects the rest of the needle tube that is not protected by the first cap.

11 Claims, 10 Drawing Sheets

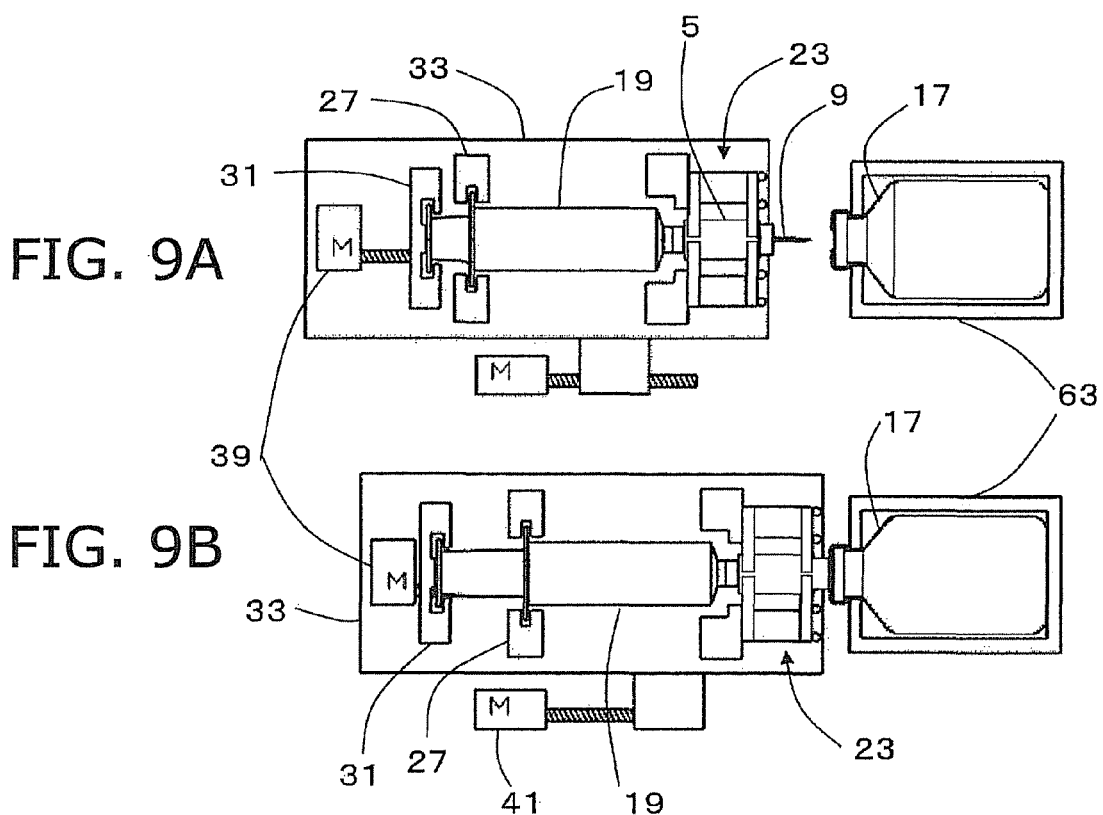

INJECTION NEEDLE PROTECTOR, INJECTION NEEDLE UNIT, AND INJECTOR TO WHICH THIS INJECTION NEEDLE UNIT IS MOUNTED

BACKGROUND OF THE INVENTION

1. Technical Field

The present invention relates to an injection needle protector that protects an injection needle, to an injection needle unit, and to an injector to which this injection needle unit is mounted. More particularly, it relates to an injection needle protector for being held by an injector holder, to an injection needle unit, and to an injector to which this injection needle unit is mounted.

2. Description of the Related Art

The job of inserting the needle tube of an injector into a vial or other such drug container filled with a drug, which is performed by a nurse or physician, is time-consuming and requires accuracy. In particular, mixing different drugs often entails numerous such insertions, so there is a need for accuracy and a reduction in the work involved. Also, when radioactive pharmaceuticals, anti-cancer drugs, and other such hazardous pharmaceuticals are handled, this work must be carried out in a sterile fashion. Accordingly, the insertion work needs to be automated with an apparatus.

For example, an injector used in an apparatus that performs puncture work, such as a drug mixing apparatus, has an injection needle unit equipped with a needle tube and a needle base that is connected to one end of this needle tube, a barrel that is connected to the needle base, and a plunger. To prevent accidental puncture, a substantially cylindrical injection needle protector is fitted to the needle base. With an injector such as this, the needle protector is left in place while the injector is introduced into the drug mixing apparatus, and the barrel of the injector is held by an injector holder that constitutes part of the drug mixing apparatus or other such apparatus, which fixes the injector to the injector holder (Japanese translation of PCT international application No. 2010-510513).

SUMMARY OF THE INVENTION

Problem to be Solved by the Invention

With prior art, however, a new configuration is needed for accurately inserting the needle tip of the injector into the mouth of the container holding the drug, and this makes the apparatus more complicated.

Specifically, accurate puncture requires that the injector be fixed in the injector holder, but the injector holder cannot directly hold the needle tube from the standpoint of hygiene. Accordingly, the injector is fixed to the injector holder by holding the barrel of the injector.

However, even though the barrel is fixed, there may be variance in the position of the needle tip in the radial direction of the needle tube depending on how well the barrel tip and the needle base are joined, how well the needle base and the needle tube are joined, and manufacturing error in the barrel, the needle base, the needle tube, etc.

As a result, accurate insertion of the needle tip of the injector into the mount of the drug container requires a camera, electrical control, and so forth to ascertain the position of the needle tip and the inclination of the needle tube, and this ends up making the injector holder, and the apparatus that includes it, more complicated.

In view of this, it is an object of the present invention to provide an injection needle protector, an injection needle unit, and an injector to which this injection needle unit is mounted, with which the needle tip of an injector can be accurately inserted into a drug container without making a drug mixing apparatus more complicated.

Means for Solving Problem

To achieve this object, the present invention is an injection needle protector that protects a needle tube connected to a needle base by covering the needle tube, said injection needle protector comprising a first cap that protects the needle tube on the needle base side and is also held by an injector holder, and a second cap that protects the rest of the needle tube that is not protected by the first cap. The first cap has a supporter that supports the needle tube from the outer periphery.

Consequently, the needle tip of the injector can be accurately inserted into a drug container without making the injector holder, or the apparatus that includes it, more complicated. Specifically, since an injector to which the injection needle protector is applied is fixed to the injector holder by having the first cap be held even if the second cap is removed, the needle tip of the injector can be accurately inserted into a drug container without making the injector holder, or the apparatus that includes it, more complicated.

Also, it is preferable if the supporter of the first cap is provided at the distal end of the first cap.

This allows the supporter of the first cap to support the needle tube on the needle tip side, so there is less variance, in the radial direction of the needle tube, in the position of the needle tip of the injector to which the injection needle protector is mounted, and the needle tip can be inserted more accurately into the drug container.

Also, it is preferable if a flange is provided to the first cap.

As a result, the flange prevents the drug from clinging to the side face of the first cap even if the drug should cling to the needle tube of the injector to which the injection needle protector is applied, which is more hygienic. Consequently, the drug is less apt to cling to the injector holder that holds the first cap, and there is no need for some means for rinsing off residual drug.

Also, it is preferable if the flange is provided more toward the needle tip side of the needle tube than the supporter.

This effectively suppresses the spread of drug clinging to the needle tube of the injector to which the injection needle protector is applied. Also, the first cap can be held by the injector holder over a larger region.

Also, it is preferable if the injector holder holds the part of the first cap at the supporter.

Out of the entire first cap, if the portion held by the injector holder is the supporter that touches and supports the needle tube, the holding force of the injector holder will tend to be transmitted through the supporter to the needle tube.

Also, it is preferable if the inner wall of the supporter fits snugly against the outer periphery of the needle tube.

This allows more of the holding force produced by the injector holder to be transmitted through the supporter to the needle tube.

Effects of the Invention

With the present invention, the needle tip of an injector can be accurately inserted into a drug container without making the injector holder, or the apparatus that includes it, more complicated.

BRIEF DESCRIPTION OF DRAWINGS

FIG. 9A is a front view of how an injector to which the injection needle protector in Embodiment 1 of the present invention has been applied is fixed to the injector holder and disposed opposite a vial, and FIG. 9B is a front view of how an injector to which the injection needle protector in Embodiment 1 of the present invention has been applied is fixed to the injector holder and the needle tube is inserted into the vial;

DETAILED DESCRIPTION OF THE INVENTION

Embodiment 1

Figure 1:
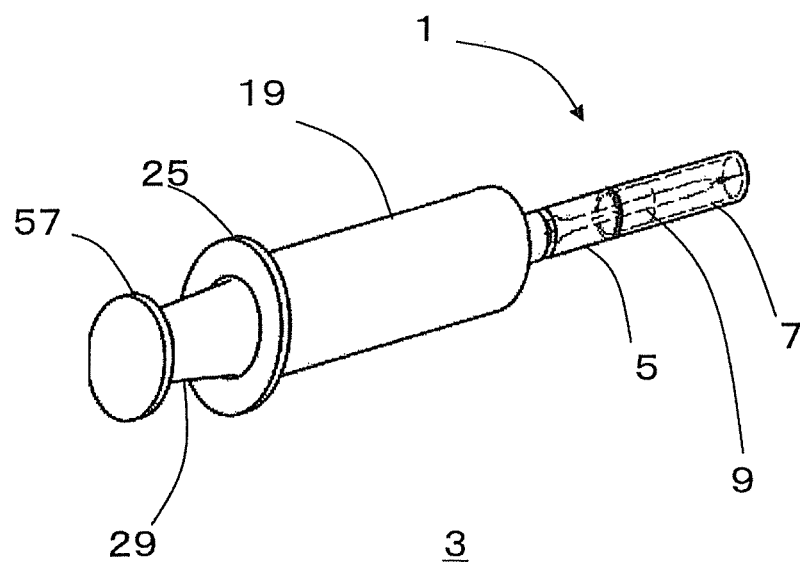
FIG. 1 is an oblique view of an injector to which is applied the injection needle protector of Embodiment 1 of the present invention.
Figure 2A:
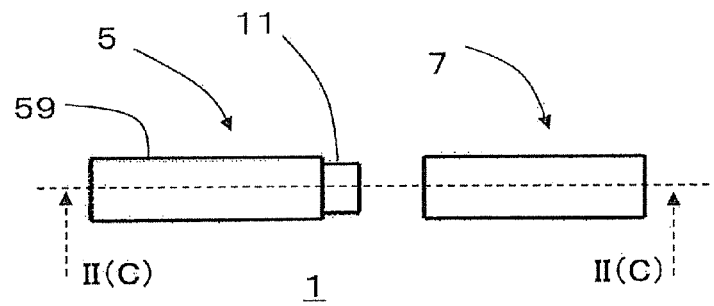
FIG. 2A is a front view of a first cap and a second cap that constitute the injection needle protector of Embodiment 1 of the present invention.
Figure 2B:
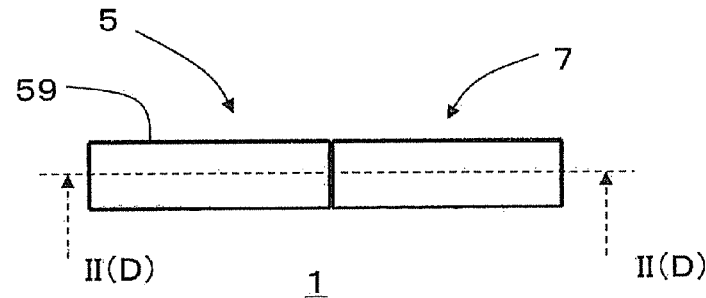
FIG. 2B is a front view of these caps connected together.
Figure 2C:
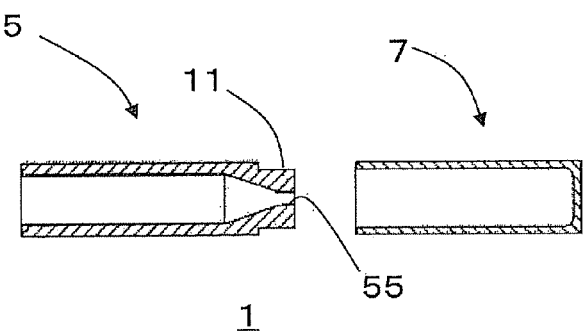
FIG. 2C is a cross section along the II(C)-II(C) line in FIG. 2A.
Figure 2D:
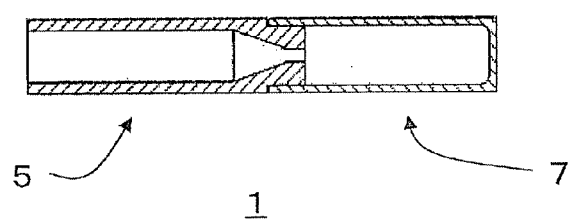
FIG. 2D is a cross section along the II(D)-II(D) line in FIG. 2B.

The injection needle protector 1 of the present invention will now be described in detail along with the drawings. FIG. 1 is an oblique view of an injector 3 to which the injection needle protector 1 of the present invention is mounted. The injector 3 is intended for use with an injector holder 21, and puncture is automatically performed when the injector 3 is fixed to the injector holder 21.

The injection needle protector 1 is made up of a first cap 5 and a second cap 7. The injector holder 21 holds the first cap 5 even when the second cap 7 is removed, allowing a needle tube 9 to be fixed at the correct position with respect to the injector holder 21. As a result, there is no need for the injector holder 21, or the drug mixing apparatus that includes it, to be made more complicated, which is the gist of the present invention.

FIGS. 2A to 2D consist of front views of the injection needle protector 1 of the present invention. The first cap 5 is made up of a cylindrical part 59 and a supporter 11 that has a smaller outside diameter than the cylindrical part 59. The cylindrical part 59 and the supporter 11 are disposed coaxially.

In the interior of the first cap 5 are formed a cylindrical space, another space that is cylindrical but has a diameter that is substantially the same as the outer periphery of the needle tube 9, receives the needle tube 9, and supports it from the outer periphery, and another space that has a tapering shape that connects the first two spaces. The center axes in the lengthwise direction of these spaces coincide with each other.

The second cap 7, which has a bottomed, cylindrical shape, is removably fitted to the first cap 5 so that its open end covers the entire supporter 11 of the first cap 5, and is positioned by the edge of the cylindrical part 59 on the supporter 11 side.

Figure 3A:
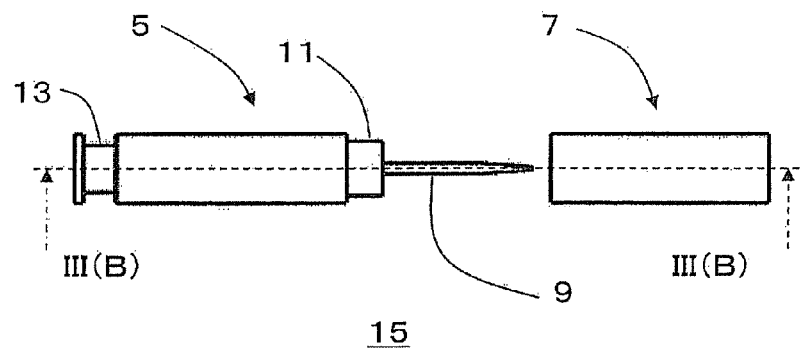
FIG. 3A is a front view of how the second cap is removed from the first cap in the injection needle unit in Embodiment 1 of the present invention.
Figure 3B:
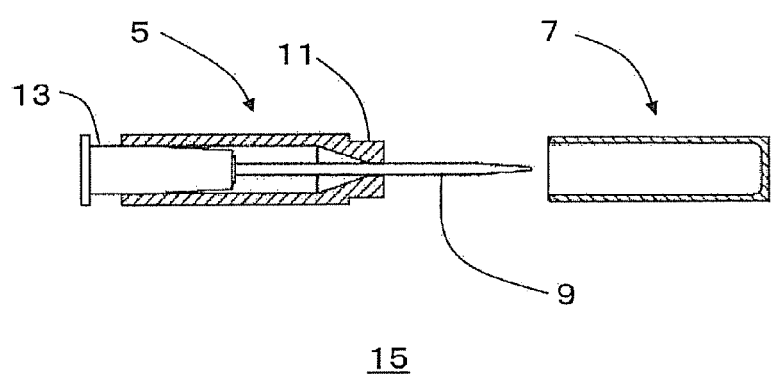
FIG. 3B is a cross section along the III(B)-III(B) line in FIG. 3A.

FIGS. 3A and 3B show an injection needle unit 15 in which this injection needle protector 1 is provided to the needle tube 9 and a needle base 13. The injection needle unit 15 here includes the needle tube 9, the needle base 13 that is connected to the needle tube 9, the first cap 5, and the second cap 7. FIG. 3B is a cross section along the III(B)-III(B) line in FIG. 3A, but the needle tube 9 and the needle base 13 are shown in front view rather than cross section.

As shown in FIGS. 3A and 3B, the needle base 13 connected to one end of the needle tube 9 is fixed by being tightened to the open end on the opposite side of the first cap 5 from the supporter 11. In this state, of the needle tube 9 from the distal end of the needle base 13 to the needle tip, the approximately center portion with respect to the lengthwise direction is supported at the outer periphery by the supporter 11. The supporter 11 and the needle tube 9 fit snugly together. That is, the inner wall 55 of the supporter 11 fits snugly against the outer periphery of the needle tube 9.

Therefore, the first cap 5 has the function of protecting the part on the needle base 13 side from the needle tube 9 that extends from the needle base 13, to the needle tube 9 that is directly supported by the supporter 11, and if the first cap 5 is fixed, it has at the same time the function of fixing the needle tube 9 as well. The needle tube 9 and the needle base 13 here may be inserted from the open bottom face side of the first cap 5 (molded in a metal mold) and fixed to the stationary first cap 5, but the needle tube 9 and the needle base 13 may be squeezed by flaps of the first cap 5 that has been split in two (or more) pieces in the lengthwise direction, and the flaps press-fitted so that the fixing is accomplished while forming the cylindrical shape of the first cap 5.

The second cap 7 covers the remaining portion of the needle tube 9 that is not protected by the first cap 5, that is, the needle tube 9 from the supporter 11 to the needle tip. The length of the needle tube 9 covered by the second cap 7 here is adjusted to a length that allows mixing using a vial or other such drug container 17.

Figure 4:
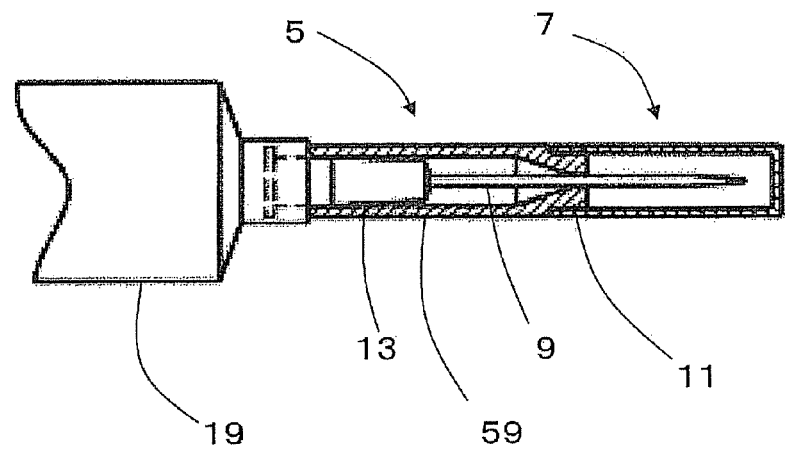
FIG. 4 is a partial cross section of the main components of an injector to which the injection needle unit in Embodiment 1 of the present invention has been applied.

FIG. 4 shows how the injection needle unit 15 is connected to the distal end part of the barrel 19 of the injector 3. This connection is made by inserting the portion of the needle base 13 not covered by the first cap 5 into the opening at the distal end of the barrel 19. This fixing can be accomplished by a known method, such as a threaded structure.

Figure 5:
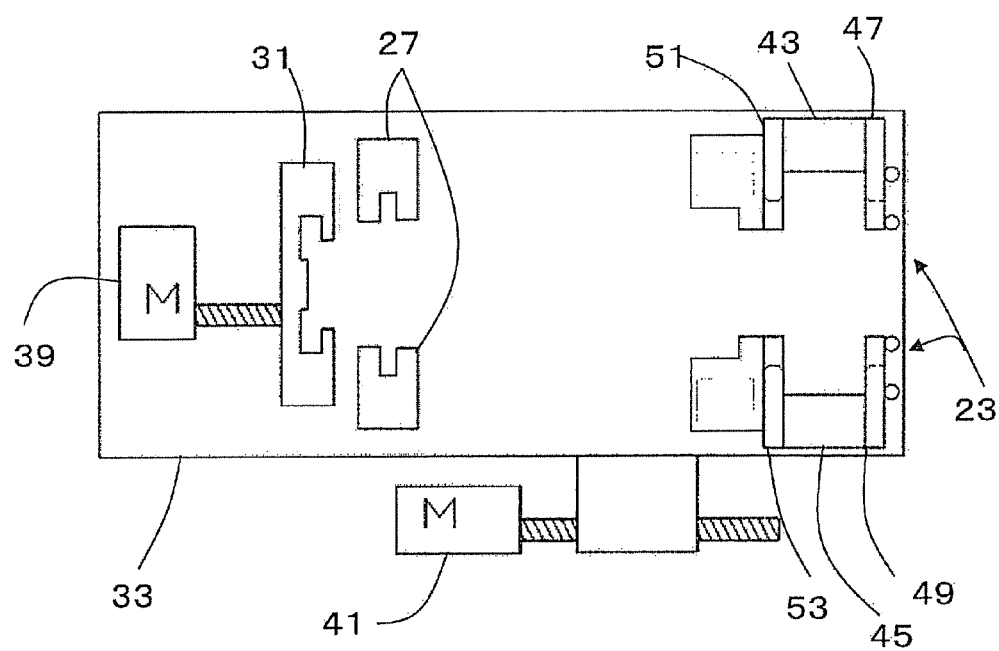
FIG. 5 is a front view of an injector holder that fixes the injector to which the injection needle protector in Embodiment 1 of the present invention has been applied.

Next, the injector holder 21 used to fix the injector 3 to which the injection needle protector 1 has been mounted will be described. The injector holder 21 holds the injector 3 so that the injector 3 can be subjected to some kind of action, and may have a partial configuration of a manipulator that holds the injector 3. As shown in FIG. 5, the injector holder 21 is primarily made up of a cap fixing component 23 that fixes the first cap 5 of the injection needle protector 1, a flange holder 27 for holding a flange 25 provided to the end of the barrel 19, and a plunger holder 31 that holds a plunger 29 of the injector 3. These components are disposed on a base 33. The injector holder 21 also comprises motors 35, 37, 39 and 41 that move the cap fixing component 23, the plunger holder 31, and the base 33, respectively.

Figure 6:
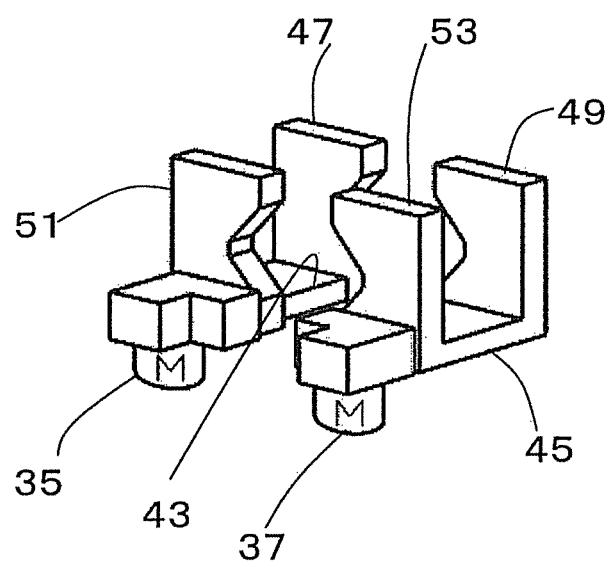
FIG. 6 is an oblique view of a cap fixing component that constitutes part of the injector holder that fixes the injector to which the injection needle protector in Embodiment 1 of the present invention has been applied.

The cap fixing component 23 is driven by the motors 35 and 37, and fixes the first cap 5 by sandwiching it from both sides. FIG. 6 is an oblique view of the cap fixing component 23. As shown in this drawing, two cap distal end fixing plates 47 and 49 for fixing the distal end of the first cap 5 are provided vertically and opposite each other on horizontal plates 43 and 45 driven separately by the motors 35 and 37. The opposing faces of these cap distal end fixing plates 47 and 49 each have a substantially trapezoidal notched formed for fixing the first cap 5.

Cap proximal end fixing plates 51 and 53 are disposed opposite each other and parallel to the cap distal end fixing plates 47 and 49 on the horizontal plates 43 and 45. A substantially trapezoidal notch is also formed in each of the cap proximal end fixing plates 51 and 53, the proximal end of the first cap 5 is received by these notches, and is fixed such that it is sandwiched from both sides.

As shown in FIG. 5, the flange holder 27 is provided perpendicular to the base 33 and consists of two similarly shaped plates, each of which has a horizontal cross section with an approximate U shape, having their grooves opposite each other. The flange holder 27 accommodates the edges of the flange 25 provided to the barrel 19 of the injector 3 in these grooves, and thereby has the function of holding the barrel 19, but all that is necessary is that movement of the injector 3 in the lengthwise direction be restricted, and there is no need to restrict movement in a direction perpendicular to this lengthwise direction. Therefore, the flange holder 27 in this example is not movable with a motor or the like.

The plunger holder 31 is disposed perpendicular to the base 33 on the rear side of the flange holder 27. The term "rear" as used in this Specification encompasses the meaning of "more to a flange 57 side of the plunger 29." The flange 57 provided to the end of the plunger 29 of the injector 3 is received by the plunger holder 31, the flange 57 of the plunger 29 is fitted into these grooves, and the motor 39 is controlled so that plunger 29 is moved back and forth within the barrel 19. This moves the drug (not shown) in and out of the interior of the barrel 19.

The operation of the injector holder 21 will be described through reference to the injector 3 to which the injection needle protector 1 has been mounted. First, the operation up to the point when the injector 3 is fixed to the injector holder 21 will be described.

Figure 7A:
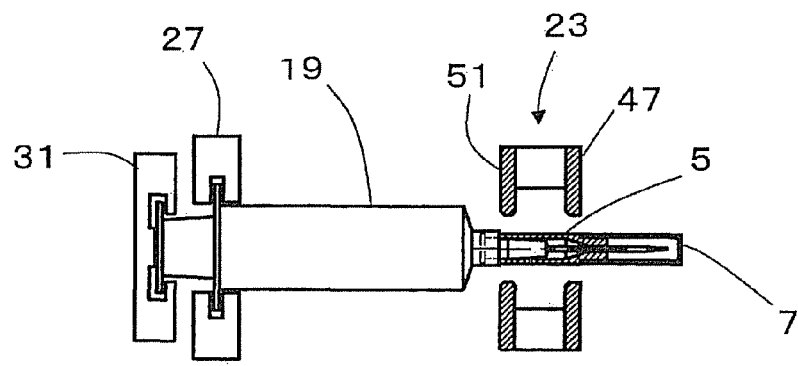
FIG. 7A is a partial cross section of a front view showing how the injector to which the injection needle protector in Embodiment 1 of the present invention has been applied is mounted in the injector holder.
Figure 7B:
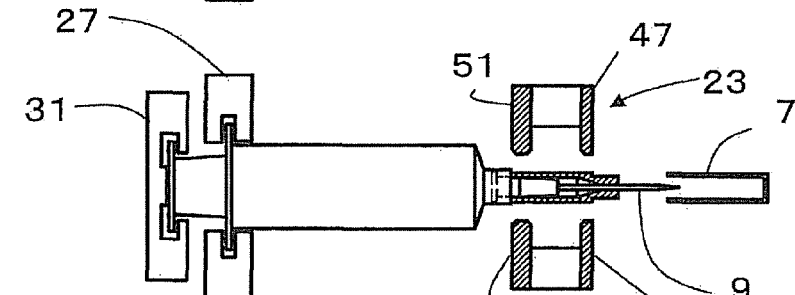
FIG. 7B is a partial cross section of a front view showing how the injector to which the injection needle protector in Embodiment 1 of the present invention has been applied is mounted in the injector holder and the second cap is removed.
Figure 7C:
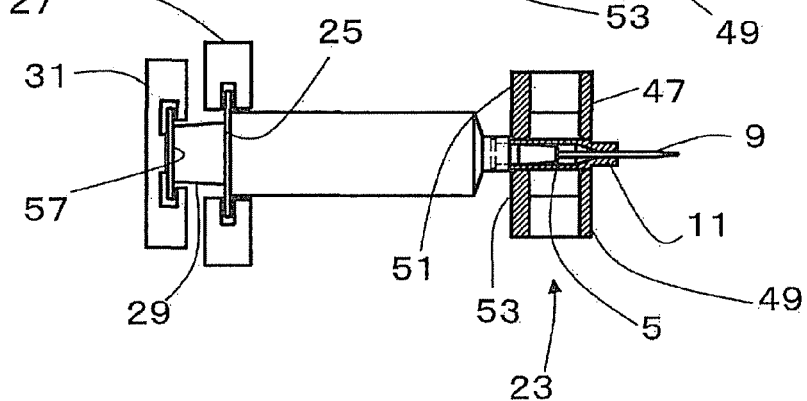
FIG. 7C is a partial cross section of a front view showing how the injector to which the injection needle protector in Embodiment 1 of the present invention has been applied is fixed to the injector holder.

FIGS. 7A, 7B, and 7C show in time series the operation in which the injector 3 is fixed to the injector holder 21, and show horizontal cross sections of the first cap 5, the second cap 7, and the cap fixing component 23.

FIG. 7A shows the state after the injector 3 has been installed in the injector holder 21 by an injector installation mechanism of a drug mixing apparatus. The flange 25 of the barrel 19 and the flange 57 of the plunger 29 are fixed into the grooves of the plunger holder 31 and the flange holder 27, respectively, and are held so that movement in the lengthwise direction of the injector 3 is restricted. At this stage, the cap fixing component 23 is open, so the needle tube 9 is not fixed at the proper position. The plunger 29 is in a state in which it has been inserted all the way into the barrel 19.

After this, as shown in FIG. 7B, the second cap 7 is removed from the first cap 5 by a mechanism of the drug mixing apparatus (not shown).

Then, as shown in FIG. 7C, the cap fixing component 23 is operated to fix the needle tube 9. The cap fixing component 23 fixes the first cap 5 by sandwiching the distal end and proximal end of the first cap 5 of the injection needle unit 15 from both sides with the two motors 35 and 37.

More precisely, this fixing involves sandwiching the front portion of the cylindrical part 59 closer to the portion connected to the supporter 11, with the two cap distal end fixing plates 47 and 49. Therefore, the needle tube 9 is fixed with respect to the injector holder 21 via the supporter 11 of the first cap 5.

Also, the rear portion of the wide-diameter cylindrical part 59 of the first cap 5 is fixed so as to be sandwiched from both sides by the two cap proximal end fixing plates 51 and 53. Consequently, the needle tube 9 is fixed more securely with respect to the injector holder 21.

Figure 8:
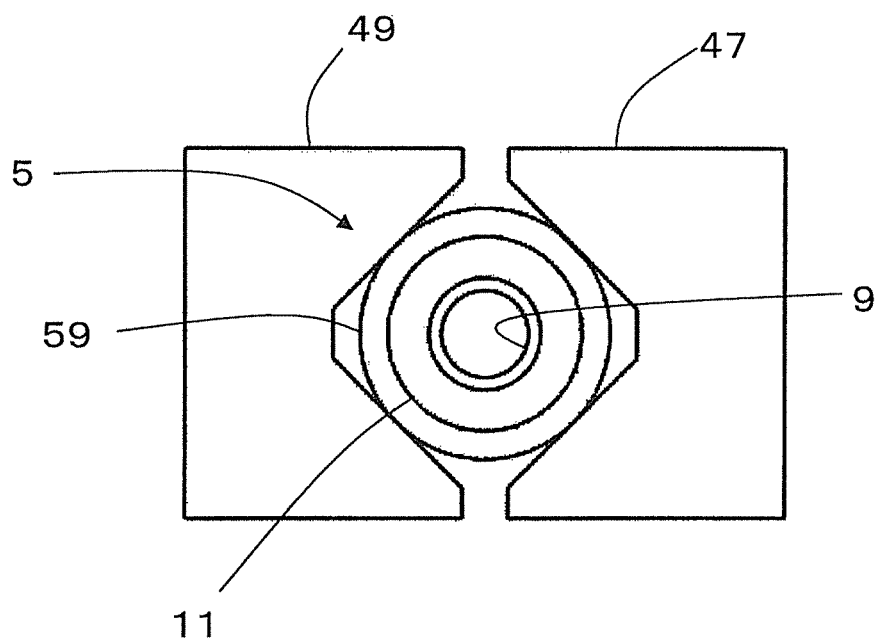
FIG. 8 is a reference diagram, as seen from the needle tip side, of how the injector from which the second cap has been removed is held by the injector holder.

FIG. 8 shows a state in which the cylindrical part 59 of the first cap 5 is fixed by the cap distal end fixing plates 47 and 49. As shown here, the cylindrical part 59 is sandwiched between the opposing, substantially trapezoidal notches of the cap distal end fixing plates 47 and 49, so that the cap distal end fixing plates 47 and 49 act on and fix at four points around the outer periphery of the cylindrical part 59.

Here, from the standpoint of transmitting more of the holding force produced by the injector holder 21 to the needle tube 9, the part of the first cap 5 that is held by the cap distal end fixing plates 47 and 49 may be the supporter 11, with direct fixing that sandwiches the outer periphery of the smaller-diameter supporter 11.

The injector holder 21 to which the injector 3 has been installed and the needle tube 9 fixed is used for mixing with a drug mixing apparatus. FIG. 9A shows an example of part of this mixing, and shows how the injector holder 21 and a container holder 63 that holds a vial 17 are disposed opposite each other so that the needle tube 9 is perpendicular to the opening of the vial 17, which has a rubber stopper (not shown).

As shown in FIG. 9B, from this state, the base 33 of the injector holder 21 is moved toward the vial 17 by a motor 41, and the needle tube 9 punctures the rubber stopper. After this, the motor 39 causes the plunger holder 31 to retract the plunger 29 of the injector 3 from the barrel 19, and the drug inside the vial 17 is moved into the barrel 19. After this, the motor 41 returns the base 33 to the position in FIG. 9A, and mixing is performed, such as injecting the drug into another vial 18.

As discussed above, the injector 3 in this example comprises the first cap 5 that protects the needle tube 9 on the needle base 13 side and is held by the injector holder 21, and the second cap 7 that protects the rest of the needle tube 9 that is not protected by the first cap 5. Since the first cap 5 has the supporter 11 that supports the needle tube 9 from its outer periphery, even if there should be error attributable to the manufacture of the barrel 19, the needle base 13, etc., or the connection between the needle base 13 and the tip of the barrel 19 or the connection between the needle base 13 and the needle tube 9, the needle tip of the injector 3 can still be accurately inserted into the drug container 17 without making the injector holder 21, or the drug mixing apparatus that includes it, more complicated.

More specifically, the cap fixing component 23 of the injector holder 21 directly fixes the first cap 5, and the holding force thus produced is transmitted to the needle tube 9, which is snugly pressed again the inner wall 55 of the supporter 11, so the needle tube 9 can be accurately fixed to the injector holder 21. This allows the needle tip to be accurately inserted into the mouth of the vial or other such drug container 17.

Also, since the second cap 7 is removably connected to the first cap 5, after the work is complete, the second cap 7 can be reconnected to the first cap 5 for protection in taking the injector 3 out of the drug mixing apparatus. This is beneficial when the drug is drawn out of the drug container 17 and into the barrel 19 for administration to the patient.

Embodiment 2

Figure 10A:
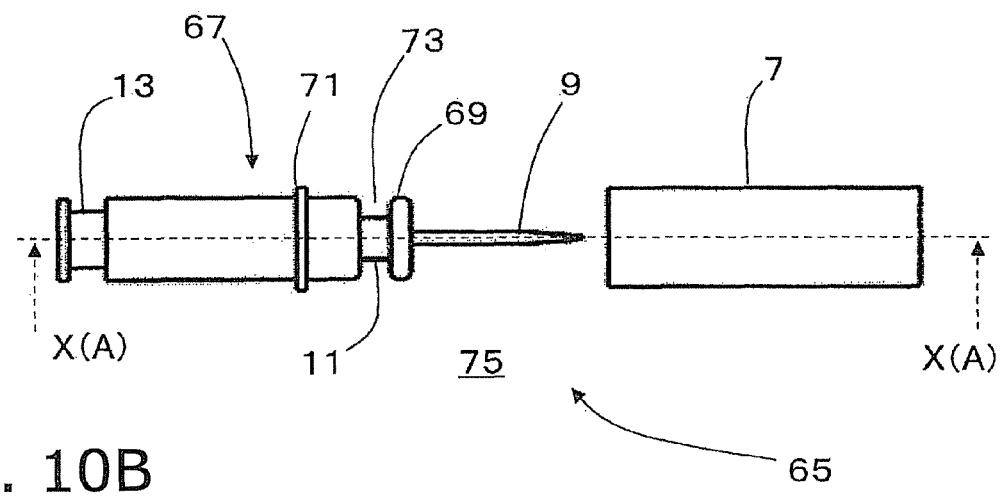
FIG. 10A is a front view of how the second cap in the injection needle unit in Embodiment 2 of the present invention is removed from the first cap.
Figure 10B:
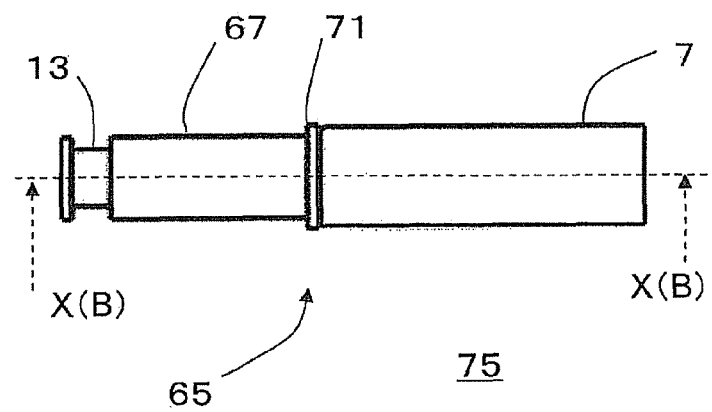
FIG. 10B is a front view of the injection needle unit in Embodiment 2 of the present invention in which the first cap and the second cap are connected together.
Figure 11A:
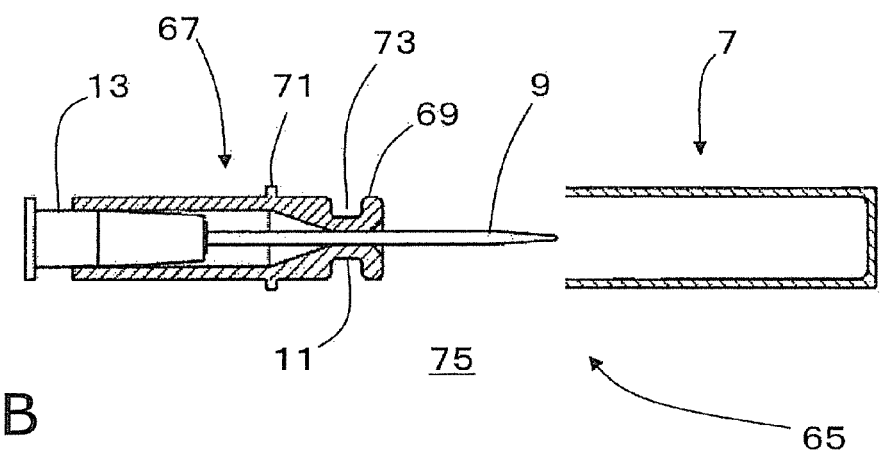
FIG. 11A is a partial cross section along the X(A)-X(A) line in FIG. 10A.
Figure 11B:
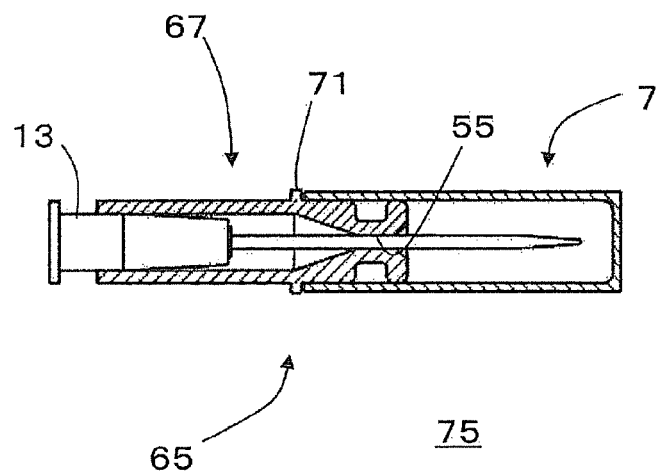
FIG. 11B is a partial cross section along the X(B)-X(B) line in FIG. 10B.

FIGS. 10A, 10B and 11A, 11B show an injection needle protector 65 of a second example as an injection needle unit 75 to which a needle tube 9 and a needle base 13 are fitted. FIGS. 10A and 10B show a first cap 67 and a second cap 7 mounted to the needle tube 9 and the needle base 13. FIGS. 11A and 11B shows the cross section of FIGS. 10A and 10B. The needle tube 9 and the needle base 13, however, are shown in front view rather than cross section. Those members that are the same here as in the first example will be numbered the same, and will not be described again.

The difference between the injection needle unit 15 of the first example and the injection needle unit 75 of the second example is the configuration of the first cap 67. Specifically, as shown in FIGS. 10A to 11B, a flange 69 is provided at the distal end of the supporter 11 of the first cap 67 in this example. Also, a ring 71 for positioning the open end of the second cap 7 when the second cap 7 is fitted to the first cap 67 is formed around the outer periphery of the cylinder of the first cap 67 further to the rear than the supporter 11.

The cylindrical supporter 11 is smaller in diameter than the wide-diameter first cap 67, and the outside diameter of the ring-shaped flange 69 is the same as the wide-diameter first cap 67. Therefore, a ring-shaped groove 73 is formed at the supporter 11 on the first cap 67.

The support of the first cap 67 by the injector holder 21 here may be accomplished by fitting the cap distal end fixing plates 47 and 49 of the cap fixing component 23 into this groove 73, or, just as in the first example, the cap distal end fixing plates 47 and 49, which are wider in diameter between the supporter 11 and the ring 71 used for positioning the open end of the second cap 7, may fix the needle tube 9 by sandwiching it from both sides.

In this example, the following effect is obtained in addition to the effect of the first example. Specifically, even if some of the drug should cling to the needle tube 9 when it punctures the drug container 17, the flange 69 will prevent this from spreading out further to the side face of the first cap 67. Accordingly, the drug will not cling to the cap fixing component 23 of the injector holder 21, so good hygiene can be maintained. Also, in connecting the second cap 7 to the first cap 67, not only is the open end of the second cap 7 positioned by the ring 71, but this ring 71 also serves as a back-up to the flange 69.

INDUSTRIAL APPLICABILITY

The present invention can be applied to any injector that needs to be inserted accurately. In particular, it can be applied to injectors used with containers of a drug mixing apparatus or the like with which the container is punctured automatically.

The invention claimed is:

1. An injection needle protector for protecting a needle tube that is connected to a needle base and which has an outer periphery, a tip, and a needle base side opposite to the tip, by covering the needle tube, said injection needle protector comprising:
   a first cap that protects the needle tube on the needle base side of the needle tube, the first cap having a supporter that supports the needle tube from the outer periphery of the needle tube, and the first cap further having a held portion at an outer periphery of the first cap for being held by a fixing portion of an injector holder,
   a second cap that protects the rest of the needle tube that is not protected by the first cap;
   wherein the second cap is removably fitted to the supporter of the first cap.

2. The injection needle protector of claim 1, wherein the first cap is removably fitted to the needle base.

3. The injection needle protector of claim 1, wherein the supporter of the first cap is provided at the distal end of the first cap.

4. The injection needle protector of claim 1, wherein a flange is provided to the first cap.

5. The injection needle protector of claim 4, wherein the flange is provided more toward the needle tip side of the needle tube than the supporter.

6. The injection needle protector of claim 1, wherein the inner wall of the supporter fits snugly against the outer periphery of the needle tube.

7. An injection needle unit comprising:
   a needle base;
   a needle tube connected to the needle base; and
   the injection needle protector of claim 1,
   wherein the injection needle protector is disposed on the needle tube with the supporter of the first cap contacting the outer periphery of the needle tube and the tip of the needle tube being enclosed by the second cap.

8. An injector, comprising:
   a barrel for holding a fluid to be injected;
   the injection needle unit of claim 7 disposed on the barrel; and
   a plunger displaceable relative to the barrel for injecting the fluid through the needle tube.

9. A combination including:
   the injector of claim 8; and
   an injector holder configured to hold the injector,
   wherein the second cap of the injection needle protector is configured to be removable from the first cap,
   wherein the injector holder includes a fixing portion which holds the first cap of the injection needle projector in a manner such that the second cap is removable from the first cap, and
   wherein the injector holder automatically performs puncture work using the needle tube.

10. The combination of claim 9, wherein the injector holder holds a part of the first cap at the supporter.

11. The combination of claim 9, wherein the injector holder positions the tip of the needle tube by holding the first cap of the injection needle protector, and
   wherein the injector holder automatically performs puncture work by displacing the tip of the needle tube relative to an object to be punctured and by displacing the plunger relative to the barrel.

* * * * *